United States Patent
Zeiner

(10) Patent No.: US 7,371,227 B2
(45) Date of Patent: May 13, 2008

(54) TROCAR SEAL ASSEMBLY

(75) Inventor: Mark S. Zeiner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 497 days.

(21) Appl. No.: 11/013,924

(22) Filed: Dec. 17, 2004

(65) Prior Publication Data

US 2006/0135972 A1   Jun. 22, 2006

(51) Int. Cl.
*A61M 5/178* (2006.01)
*A61M 5/00* (2006.01)
*F16K 51/00* (2006.01)
*F16K 15/14* (2006.01)

(52) U.S. Cl. .............. 604/167.03; 604/167.02; 604/167.04; 604/167.06; 604/247; 604/249; 251/149.1; 137/849

(58) Field of Classification Search ........... 604/164.01, 604/164.02, 164.06, 164.07, 164.11, 164.12, 604/167.01, 167.02, 167.03, 167.04, 167.06, 604/264, 244, 247, 249; 606/108, 167, 184, 606/185; 251/149.1; 137/849, 844
See application file for complete search history.

(56) References Cited

U.S. PATENT DOCUMENTS

| | | | |
|---|---|---|---|
| 3,504,699 A | 4/1970 | Grise | |
| 3,773,233 A | 11/1973 | Souza | |
| 4,436,519 A | 3/1984 | O'Neill | |
| 4,601,710 A | 7/1986 | Moll | |
| 4,610,665 A | 9/1986 | Matsumoto et al. | |
| 4,654,030 A | 3/1987 | Moll | |
| 4,902,280 A | 2/1990 | Lander | |
| 4,931,042 A | 6/1990 | Holmes et al. | |
| 4,932,633 A | 6/1990 | Johnson et al. | |
| 5,030,206 A | 7/1991 | Lander | |
| 5,053,013 A | 10/1991 | Ensminger et al. | |
| 5,104,383 A | 4/1992 | Shichman | |
| 5,203,773 A | 4/1993 | Green | |
| 5,209,737 A | 5/1993 | Ritchart et al. | |
| 5,211,634 A | 5/1993 | Vaillancourt | |
| 5,246,425 A | 9/1993 | Hunsberger et al. | |
| 5,300,033 A | 4/1994 | Miller | |
| 5,308,336 A | 5/1994 | Hart et al. | |
| 5,324,270 A | 6/1994 | Kayan et al. | |

(Continued)

FOREIGN PATENT DOCUMENTS

DE   10100756   8/2002

(Continued)

*Primary Examiner*—Nicholas D. Lucchesi
*Assistant Examiner*—Quynh-Nhu H Vu

(57) ABSTRACT

A seal assembly adapted for use in conjunction with a trocar assembly includes a plurality of seal segments, each seal segment including a peripheral edge and a seam edge. Each seal segment further includes a first section and a second section with a vertical wall connecting the first section and the second section in such a way that the first section is displaced relative to the second section such that the first section of a first seal segment may be placed upon the second section of a second seal segment with the first sections of the first and second seal segments lying in the same plane and the second sections of the first and second seal segments lying in the same plane. The seal segments are assembled in an overlapping woven arrangement to provide a complete seal body without the need for a secondary seal.

20 Claims, 4 Drawing Sheets

U.S. PATENT DOCUMENTS

| | | |
|---|---|---|
| 5,366,445 A | 11/1994 | Haber et al. |
| 5,385,552 A | 1/1995 | Haber et al. |
| 5,385,553 A | 1/1995 | Hart et al. |
| 5,441,041 A | 8/1995 | Sauer et al. |
| 5,456,284 A | 10/1995 | Ryan et al. |
| 5,467,762 A | 11/1995 | Sauer et al. |
| 5,534,009 A | 7/1996 | Lander |
| 5,542,931 A | 8/1996 | Gravener et al. |
| 5,549,565 A | 8/1996 | Ryan et al. |
| 5,569,160 A | 10/1996 | Sauer et al. |
| 5,578,016 A | 11/1996 | Zinger |
| 5,584,850 A | 12/1996 | Hart et al. |
| 5,603,702 A | 2/1997 | Smith et al. |
| 5,643,301 A | 7/1997 | Mollenauer |
| 5,720,730 A | 2/1998 | Blake, III |
| 5,725,504 A | 3/1998 | Collins |
| 5,743,884 A | 4/1998 | Hasson et al. |
| 5,800,451 A | 9/1998 | Buess et al. |
| 5,807,338 A | 9/1998 | Smith et al. |
| 5,895,377 A | 4/1999 | Smith et al. |
| 6,024,729 A | 2/2000 | Dehdashtian et al. |
| 6,080,134 A | 6/2000 | Lotti et al. |
| 6,086,603 A | 7/2000 | Termin et al. |
| 6,093,176 A | 7/2000 | Dennis |
| 6,254,529 B1 | 7/2001 | Ouchi |
| 6,270,484 B1 | 8/2001 | Yoon |
| 6,277,100 B1 | 8/2001 | Raulerson et al. |
| 6,302,852 B1 | 10/2001 | Fleming, III et al. |
| 6,352,520 B1 | 3/2002 | Miyazaki |
| 6,569,120 B1 | 5/2003 | Green et al. |
| 6,613,063 B1 | 9/2003 | Hunsberger |
| 6,685,630 B2 | 2/2004 | Sauer et al. |
| 6,702,787 B2 | 3/2004 | Racenet et al. |
| 2002/0007153 A1 | 1/2002 | Wells et al. |
| 2002/0010425 A1 | 1/2002 | Guo et al. |
| 2003/0660770 | 3/2003 | Wing et al. |
| 2004/0049173 A1 | 3/2004 | White et al. |
| 2004/0064100 A1 | 4/2004 | Smith |
| 2004/0147949 A1 | 7/2004 | Stellon et al. |
| 2004/0171990 A1 | 9/2004 | Dennis et al. |
| 2005/0077689 A1* | 4/2005 | Hueil .................. 277/628 |

FOREIGN PATENT DOCUMENTS

| | | |
|---|---|---|
| DE | 20209525 | 11/2002 |
| EP | 0339945 | 11/1989 |
| EP | 0567142 | 10/1993 |
| EP | 0568383 | 11/1993 |
| EP | 0696459 | 2/1996 |
| FR | 2667780 | 4/1992 |
| WO | WO 94/03232 | 2/1994 |
| WO | WO 00/35529 | 6/2000 |
| WO | WO 2004/033004 | 4/2004 |

* cited by examiner

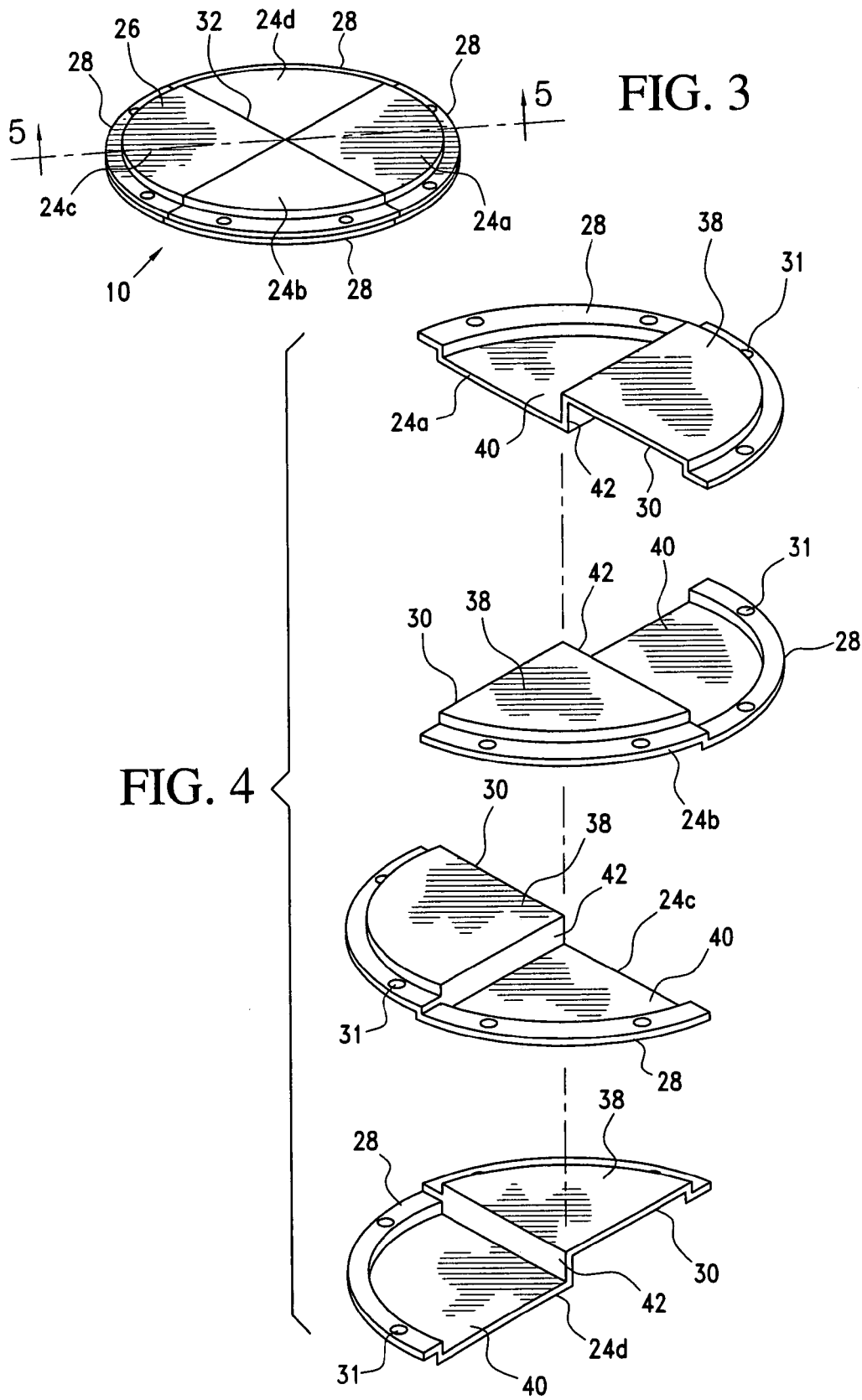

TROCAR SEAL ASSEMBLY

BACKGROUND OF THE INVENTION

1. Field of the Invention

The invention relates to trocar assemblies. More particularly, the invention relates to a trocar sealing assembly.

2. Description of the Prior Art

A trocar assembly is a surgical instrument that is used to gain access to a body cavity. A trocar assembly generally comprises two major components, a trocar sleeve, composed of a trocar housing and a trocar cannula, and a trocar obturator. The trocar cannula, having the trocar obturator inserted therethrough, is directed through the skin to access a body cavity. Once the body cavity is accessed, laparoscopic or arthroscopic surgery and endoscopic procedures may be performed. In order to penetrate the skin, the distal end of the trocar cannula is placed against the skin that has been previously cut with a scalpel. The trocar obturator is then used to penetrate the skin and access the body cavity. By applying pressure against the proximal end of the trocar obturator, the sharp point of the trocar obturator is forced through the skin until it enters the body cavity. The trocar cannula is inserted through the perforation made by the trocar obturator and the trocar obturator is withdrawn, leaving the trocar cannula as an access way to the body cavity.

The proximal end portion of the trocar cannula is typically joined to a trocar housing that defines a chamber having an open distal end portion in communication with the interior lumen defined by the trocar cannula. A trocar obturator, or other elongated surgical instruments or tools, axially extend into and are withdrawn from the trocar cannula through the proximal end portion of the chamber defined by the trocar housing.

Current trocar assemblies are commonly designed with a seal mechanism positioned within the chamber of the trocar housing. The seal mechanisms are commonly a sealing grommet or gasket through which the trocar obturator or other instruments extend. The sealing mechanism seals against the outer surface of the inserted instruments and thereby prevents fluids and insufflation gas from leaving or entering the body cavity through the trocar cannula and trocar housing. It is desired that such seals provide for good tear resistance, resistance to snagging and low friction with respect to the insertion of a device.

Seal assemblies are designed to maintain a seal before the insertion of an instrument and after the removal of the instrument. As a result, many trocar assemblies provide double sealing systems. That is, a top, or proximal seal is used to seal around the tool/instrument when inserted therethrough and a duckbill seal is provided below the top seal for sealing the trocar housing when the instrument is not present.

In contrast, other trocar assemblies employ a single sealing mechanism. Many of these trocar seal assemblies simply employ a silicone seal with a small hole slightly smaller than the smallest tool/instrument to be used in conjunction with the trocar assembly. This type of seal is often referred to as a lip seal. Surgical instruments of various diameters are passed through the lip seal. As such, these seals are often required to provide a seal for use with a full range of instrument sizes. The opening diameter of the seal is, therefore, small relative the largest diameter instruments.

In fact, it is not uncommon for lip seals to be pushed to 400% strain. By forcing these large diameter instruments through a relatively small diameter lip seal, these large diameter instruments are subjected to a significant increase in the normal force upon the shaft of the instrument. The surgeon feels this increased force as increased drag or resistance to instrument insertion/movement. It is also required that the material properties of the seal be such that the seal does not rip or tear as the seal is stretched to its limit.

As a result, a need currently exists for an improved trocar seal assembly overcoming the deficiencies of the prior art. The present invention overcomes these deficiencies by providing a seal assembly which eliminates the hoop/high stress issues associated with prior art seals and provides a seal assembly which may be utilized either with a single seal assembly (reducing the overall complexity of the trocar assembly) or as an outer gasket in a multi-seal system.

SUMMARY OF THE INVENTION

It is, therefore, an object of the present invention to provide a seal assembly adapted for use in conjunction with a trocar assembly. The seal assembly includes a plurality of seal segments, each seal segment including a peripheral edge and a seam edge. Each seal segment further includes a first section and a second section with a vertical wall connecting the first section and the second section in such a way that the first section is displaced relative to the second section such that the first section of a first seal segment may be placed upon the second section of a second seal segment with the first sections of the first and second seal segments lying in the same plane and the second sections of the first and second seal segments lying in the same plane. The seal segments are assembled in an overlapping woven arrangement to provide a complete seal body without the need for a secondary seal.

It is also an object of the preset invention to provide a trocar assembly including trocar cannula having a proximal end and distal end and a trocar housing coupled to the proximal end of the trocar cannula for receiving and guiding an obturator through the trocar cannula. The trocar housing includes an open proximal end portion defining an opening provided with a seal assembly as described above.

It is another object of the present invention to provide a trocar assembly including a trocar cannula having a proximal end and distal end and a trocar housing coupled to the proximal end of the trocar cannula for receiving and guiding an obturator through the trocar cannula. The trocar housing includes an open proximal end portion defining an opening provided with a proximal seal assembly and a distal seal assembly. The proximal seal assembly includes a plurality of seal segments, each seal segment including a peripheral edge and a seam edge. Each seal segment further includes a first section and a second section with a vertical wall connecting the first section and the second section in such a way that the first section is displaced relative to the second section such that the first section of a first seal segment may be placed upon the second section of a second seal segment with the first sections of the first and second seal segments lying in the same plane and the second sections of the first and second seal segments lying in the same plane. The seal segments are assembled in an overlapping woven arrangement to provide a complete seal body without the need for a secondary seal.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 3 is a perspective view of a proximal seal in accordance with the present invention.

FIG. 4 is an exploded view of the proximal seal shown in FIG. 3.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to FIGS. 1 to 5, a proximal seal assembly 10 for a trocar assembly 12 is disclosed. The seal assembly 10 provides for improved resistance to tearing by reducing the likelihood for tenting to occur. As those skilled in the art will appreciate, tenting occurs when a seal is stretched and thinned out, for example, by an instrument passing through the seal, thus providing an area of weakness which may be easily punctured. As those skilled in the art will certainly appreciate, the present seal assembly 10 is adapted for use with a variety of trocar assemblies. In addition, the present seal assembly 10, although described as being a proximal seal assembly in a dual seal system may be utilized in a single seal system.

Figure 1:
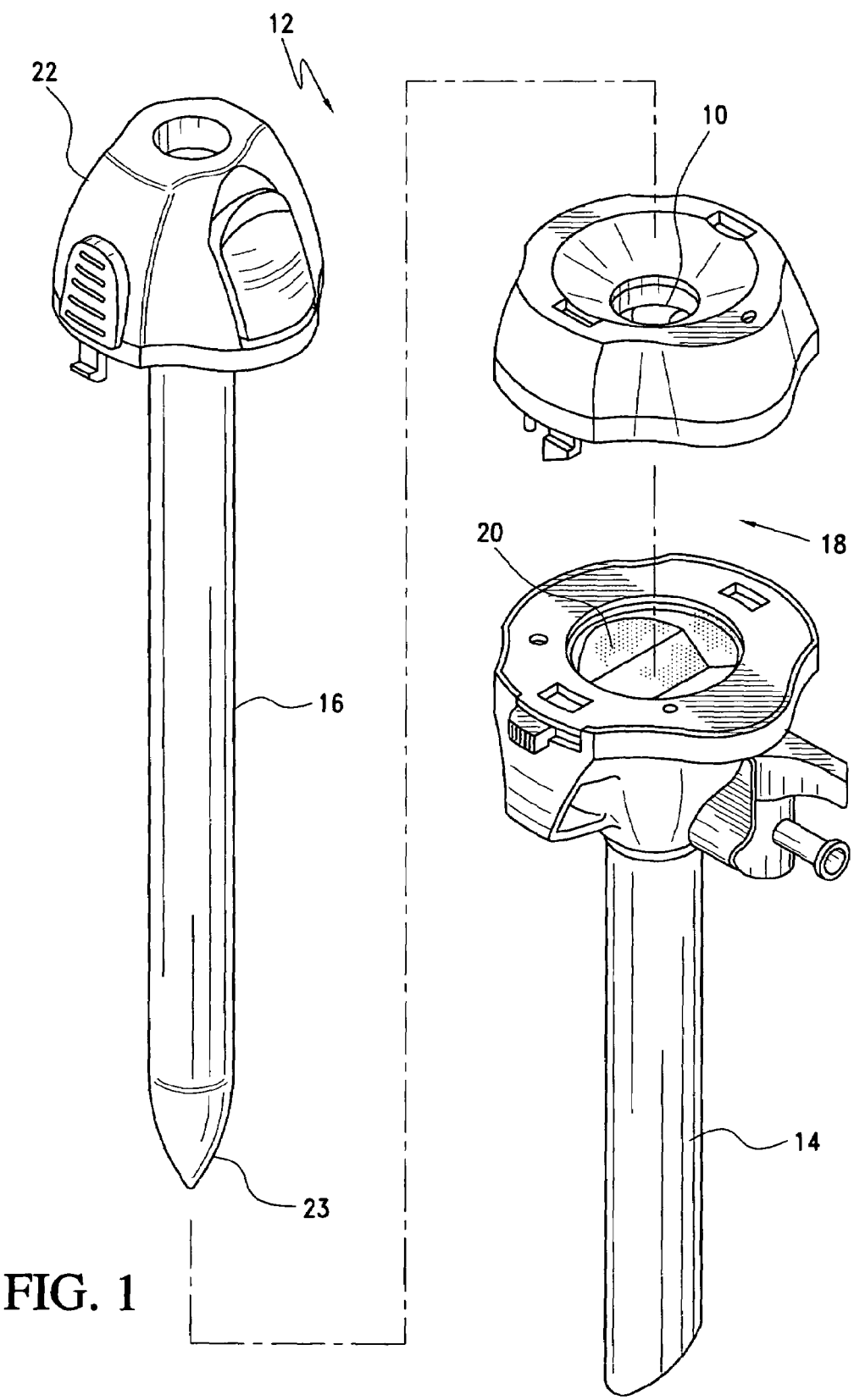
FIG. 1 is an exploded view of a trocar assembly employing a proximal seal in accordance with the present invention.
Figure 2:
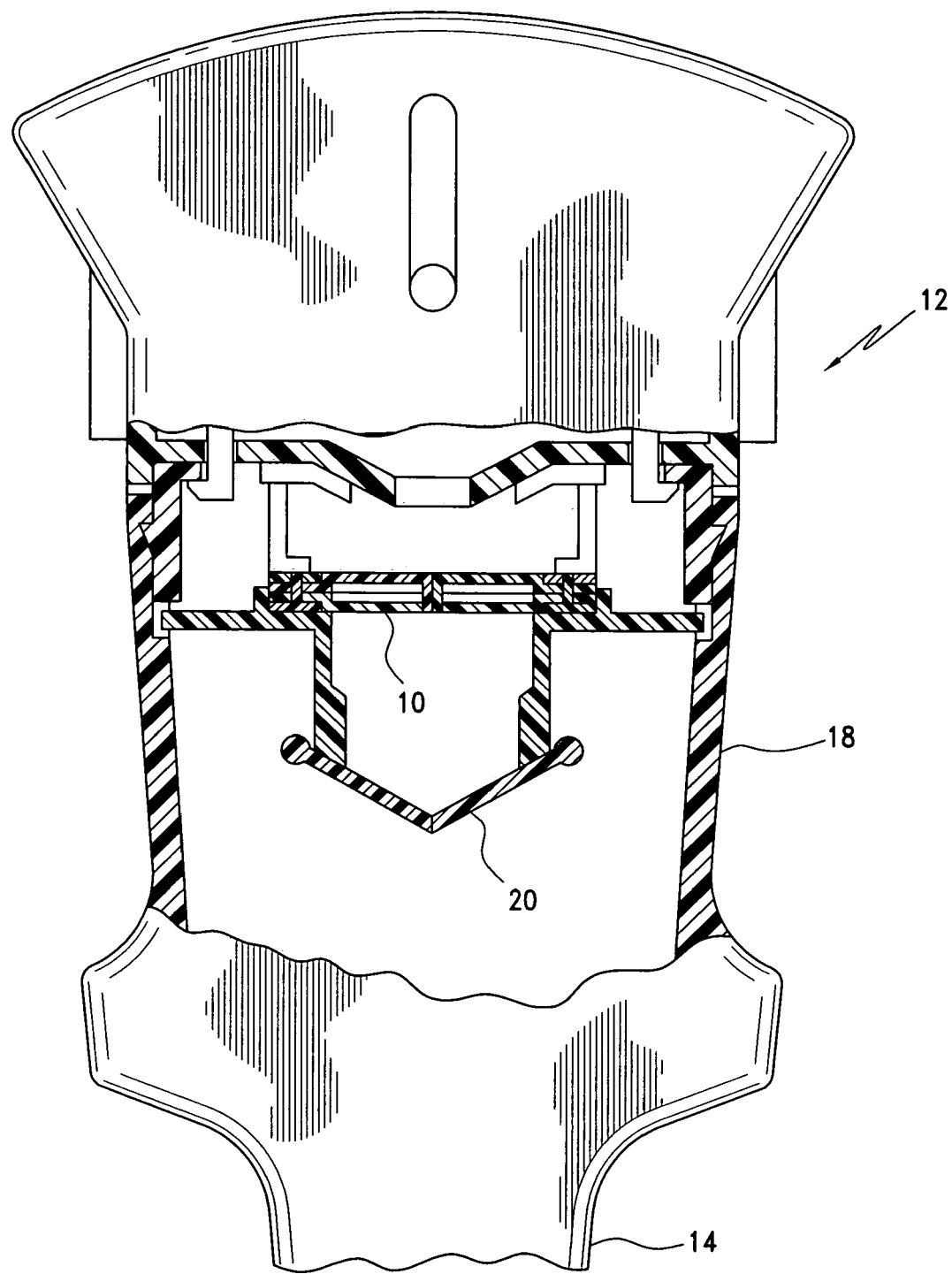
FIG. 2 is a cross sectional view of an alternate trocar housing employing a proximal seal in accordance with the present invention.

The present seal assembly 10 is adapted for use with a variety of trocar assemblies (see FIGS. 1 and 2). For example, the seal assembly 10 is adapted for use with low cost surgical trocar assemblies utilized for minimally invasive endoscopic surgical procedures, including but not limited to, laparoscopic and arthroscopic surgical procedures. Such surgical trocar assemblies are disposable and are intended to be used as a single patient use only device.

Apart from the proximal seal assembly 10 in accordance with the present invention, the general structure of the trocar assembly 12 does not form part of the present invention. For example, and by way of explaining the present seal assembly 10, the trocar assembly may take the form of those disclosed in U.S. Pat. Nos. 5,827,228, 5,947,930, 4,535,773; 5,224,952; 5,256,149; 5,314,417; 5,387,197; 5,248,298; 5,330,437; 5,399,167; 5,066,288; 5,215,526 and 5,267,965 all of which are incorporated herein by reference.

With that in mind, and by way of example, the trocar assembly 12 includes a trocar cannula 14, a trocar obturator 16, and a trocar housing (or handle) 18. The trocar cannula 14 defines an interior lumen having an open distal end portion and an open proximal end portion. The proximal end portion extends into and is mounted in the distal end portion of trocar housing 18. The trocar housing 18 has an open proximal end portion that defines an opening. The opening is provided with a proximal seal assembly 10 constructed in accordance with the present invention and described in detail hereinbelow. The opening is further provided with a duckbill seal assembly 20 positioned beneath the proximal seal assembly 10. The trocar obturator 16 is slidably and removably extendable within the trocar cannula 14 and is inserted into the trocar housing 18 and the trocar cannula 14 through the seal assembly 10 and opening of the trocar housing 18. An obturator handle 22 is provided at the proximal end of the trocar obturator 16 and a sharpened point or blade 23 is formed at the distal end thereof. As is well known in the art, the seal assembly 10 cooperates with the trocar obturator 16, or another surgical instrument extending through the trocar cannula 14, to sealingly engage the outer surface thereof and thereby preclude the passage of fluids through. the trocar housing 18.

Figure 5:
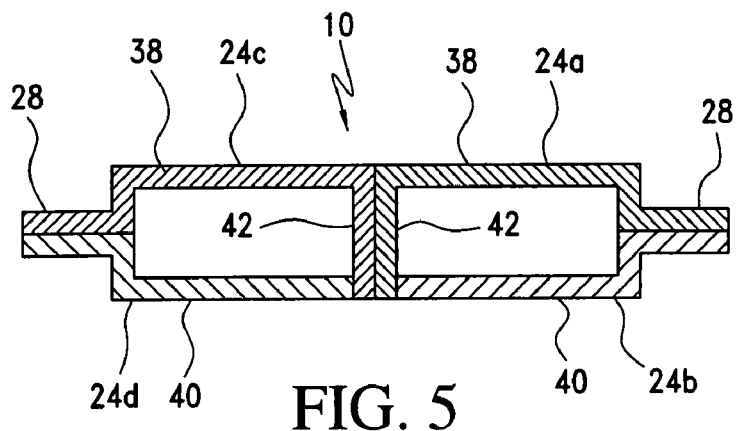
FIG. 5 is a cross sectional view of the proximal seal along the line 5-5 in FIG. 3.

Referring to FIGS. 3, 4 and 5, a preferred embodiment of the seal assembly 10 is disclosed. In accordance with a preferred embodiment of the present invention, the seal assembly 10 is composed of multiple overlapping seal segments 24 assembled in a woven arrangement to provide a complete seal body 26 without the need for a secondary seal. The present seal assembly 10 further minimizes leakage between the seal assembly 10 and an inserted instrument by providing a plurality of overlapping seal segments 24. As was discussed above, the seal assembly 10 is disclosed herein as a proximal seal assembly of a dual seal system, although the present seal assembly could readily be utilized in a single seal system.

In particular, four seal segments 24 are arranged to create the seal body 26 of the seal assembly 10. While four seal segments 24 are utilized in accordance with a preferred embodiment of the present invention, the seal body 26 may ultimately be formed with different numbers of seal segments without departing from the spirit of the present invention.

Each seal segment 24 is semicircular. Each of these seal segments 24 includes a substantially round peripheral edge 28 and a straight shaped edge 30 which ultimately defines the seam edge 32. In accordance with a preferred embodiment of the present invention, the outer peripheral edge 28 of each seal segment 24 defines an arc of approximately 180 degrees. The outer peripheral edge 28 further includes a ridge adapted for positioning within trocar housing 18. The outer peripheral edge 28 further includes a series of apertures 31 which cooperates with upper and lower retaining members (not shown) to securely attach the seal segments 24 and ultimately complete the seal assembly 10. As will be apparent based upon the following disclosure, the use of multiple seal segments 24 defining an arc of approximately 180 degrees results in a reduction in hoop stresses by providing a seal assembly 10 which employs a plurality of expanding and contracting seal segments 24 to seal about a trocar obturator 16 or other instrument inserted therethrough.

Each seal segment 24 includes a first section 38 and a second section 40. A vertical wall 42 connects the first and second sections 38, 40. More specifically, the first section 38 and the second section 40 of each seal segment 24 are offset in such a way that the first section 38 of a first seal segment 24 may be placed upon the second section 40 of a second seal segment 24 with the first sections 38 of the first and second seal segments 24 lying in substantially the same plane and the second sections 40 of the first and second seal segments lying in substantially the same plane.

In this way, the four individual seal segments 24a-d are combined in a woven arrangement to create a complete seal body 26, which fully seals without the need for a secondary seal. That is, the seal body 26 is assembled by placing the first section 38 of a first seal segment 24a upon the second section 40 of a second seal segment 24b. The first section 38 of the second seal segment 24b is subsequently placed upon the second section 40 of a third seal segment 24c, the first section 38 of the third seal segment 24c is placed upon the second section 40 of a fourth seal segment 24d and the first section 38 of the fourth seal segment 24d is placed upon the second section 40 of a first seal segment 24a.

The vertical walls 42 incorporated into each of the seal segments 24 permit expansion. In particular, the vertical walls 42 provide for expansion from the center access of the seal assembly 10. This allows for greater expansion of the seal material and ultimately the central opening. The utilization of the vertical walls 42 with first and second sections 38, 40, creates two separate sealing surfaces which are separated with a hollow air space therebetween; that is, the overlapping first and second sections 38, 40 function as two distinct sealing surfaces despite the fact all of the seal segments 24 are woven together to form a single seal body 26. Each seal segment 24 overlaps the next such that each seal segment 24 exposes only 90° of surface area when viewed from the top or bottom side of the seal assembly 10.

Figure 6:
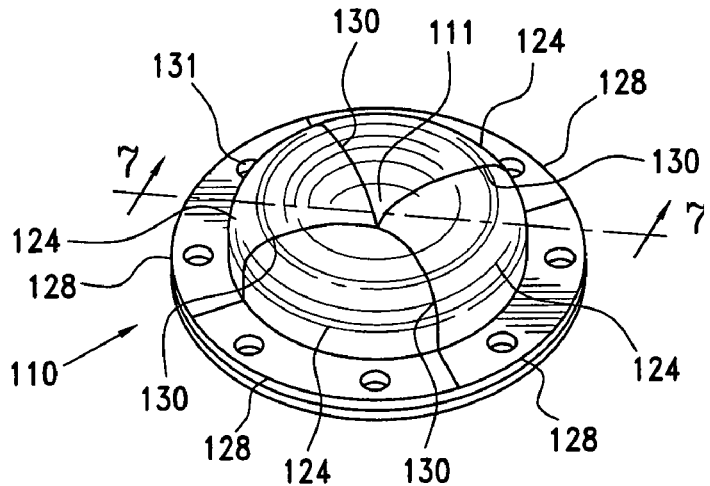
FIG. 6 is a perspective view of an alternate proximal seal in accordance with the present invention.
Figure 7:
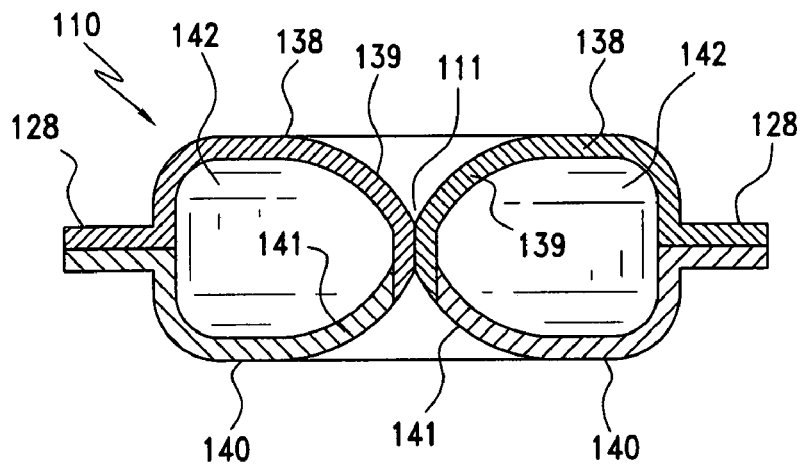
FIG. 7 is a cross section view of the proximal seal along the line 7-7 in FIG. 6.

In accordance with an alternate embodiment, and with reference to FIGS. 6 and 7, the seal assembly 110 is slightly modified for the creation of a cone shaped introducer face 111 in the center of the seal assembly 110. The cone shaped introducer face 111 provides a guide for helping an instrument enter the center of the seal assembly 110.

In particular, this embodiment includes four overlapping seal segments 124 assembled in a woven arrangement to provide a complete seal body 126 without the need for a secondary seal. As with the prior embodiment, each seal segment 124 is semicircular. Each of the seal segments 124 includes a substantially round peripheral edge 128 and a straight edge 130 which defines the seam edge 132. In accordance with a preferred embodiment of the present invention, the outer peripheral edge 128 of each seal segment 124 defines an arc of approximately 180 degrees. The outer peripheral edge 128 further includes a ridge adapted for positioning within the internal housing of a trocar housing 118. The outer peripheral edge 128 further includes a senres of apertures 131 which function as a means of attachment for the seal segments 124 and ultimately the seal assembly 110. As will be apparent based upon the following disclosure, the use of seal segments 124 defining an arc of approximately 180 degrees, results in a reduction in hoop stresses.

Each seal segment 124 includes a first section 138 and a second section 140. A vertical wall 142 connects the first and second sections 138, 140. More specifically, the first section 138 and the second section 140 of each seal segment 124 are offset in such a way that the first section 138 of a first seal segment 124 may be placed upon the second section 140 of a second seal segment 124 with the first sections 138 of the first and second seal segments 124 lying in the same plane and the second sections 140 of the first and second seal segments 124 lying the same plane.

Both the first and second sections 138, 140 of each seal segment include a central curved portion 139, 141. In particular, the first section 138 includes a curved portion 139 which is curved toward the second section 140 as the first section 138 extends from the outer peripheral edge 128 toward the point where the vertical wall 142 meets the straight edge 130 of the seal segment 124. Similarly, the second section 140 includes a curved portion 141 which is curved toward the first section 138 as the second section 140 extends from the outer peripheral edge 128 toward the point where the vertical wall 142 meets straight edge 130 of the seal segment 124.

In use, and as with the prior embodiment, the seal material is moved aside as the instrument is inserted into the center of the seal assembly 110. However, the curved portions of the first and second sections 138, 140 function to guide the instrument toward the center of the seal assembly 110.

Both embodiments are ultimately held together through the application of retaining members (not shown) to both the top and bottom surface of the assembled seal body 26, 126. Retaining members are well known to those skilled in the art and a variety of retaining members may be employed within the spirit of the present invention.

As briefly mentioned above, by providing a seal assembly 10, 110 in accordance with the present invention a secondary seal (that is, flap door or duckbill) is not required. In addition, the present seal assembly 10, 110 requires less stringent material requirement, eliminate hoop stress around large tools, reduces seal tear issues and provides a lead-in for the tool/instrument (when the cone shaped face embodiment is employed).

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A seal assembly adapted for use in conjunction with a trocar assembly, the seal assembly comprising:
   a plurality of seal segments, each seal segment includes a peripheral edge and a seam edge; each seal segment further includes a first section and a second section with a vertical wall connecting the first section and the second section in such a way that the first section is displaced and offset relative to the second section such that the first section of a first seal segment may be placed upon the second section of a second seal segment with the first sections of the first and second seal segments lying in the same plane and the second sections of the first and second seal segments lying in the same plane, wherein the vertical walls of the seal segments, with the respective first sections and second sections, create two separate sealing surfaces which are separated with an air space therebetween;
   wherein the seal segments are assembled in an overlapping woven arrangement to provide a complete seal body without the need for a secondary seal.

2. The seal assembly according to claim 1, wherein four seal segments are assembled to create the seal assembly.

3. The seal assembly according to claim 1, wherein each of the seal segments is substantially semi-circular.

4. The seal assembly according to claim 1, wherein the peripheral edge of each seal segment defines an arc of approximately 180 degrees.

5. The seal assembly according to claim 1, wherein the peripheral edge of each seal segment includes a series of apertures which function as a means of attachment for the seal segments and ultimately the seal assembly.

6. The seal assembly according to claim 1, wherein the seal assembly includes four individual seal segments combined in a woven arrangement by placing a first section of a first seal segment upon a second section of a second seal segment, placing a first section of the second seal segment upon a second section of a third seal segment, placing a first section of the third seal segment upon a second section of a fourth seal segment and placing a first section of the fourth seal segment upon a second section of the first seal segment.

7. The seal assembly according to claim 1, wherein each seal segment includes a central curved portion.

8. The seal assembly according to claim 1, wherein each seal segment is an elastomer of a cross linked polymer.

9. A trocar assembly, comprising:
a trocar cannula including a proximal end and distal end;
a trocar housing coupled to the proximal end of the trocar cannula for receiving and guiding an obturator through the trocar cannula, the trocar housing includes an open proximal end portion defining an opening provided with a seal assembly;
the seal assembly includes:
a plurality of seal segments, each seal segment includes a peripheral edge and a seam edge;
each seal segment further includes a first section and a second section with a vertical wall connecting the first section and the second section in such a way that the first section is displaced and offset relative to the second section such that the first section of a first seal segment may be placed upon the second section of a second seal segment with the first sections of the first and second seal segments lying in the same plane and the second sections of the first and second seal segments lying in the same plane, wherein the vertical walls of the seal segments, with the respective first sections and second sections, create two separate sealing surfaces which are separated with an air space therebetween;
wherein the seal segments are assembled in an overlapping woven arrangement to provide a complete seal body without the need for a secondary seal.

10. The trocar assembly according to claim 9, wherein four seal segments are assembled to create the seal assembly.

11. The trocar assembly according to claim 9, wherein each of the seal segments are substantially semi-circular.

12. The trocar assembly according to claim 9, wherein the peripheral edge of each seal segment defines an arc of approximately 180 degrees.

13. The trocar assembly according to claim 9, wherein the peripheral edge of each seal segment includes a series of apertures which function as a means of attachment for the seal segments and ultimately the seal assembly.

14. The trocar assembly according to claim 9, wherein the seal assembly includes four individual seal segments combined in a woven arrangement by placing a first section of a first seal segment upon a second section of a second seal segment, placing a first section of the second seal segment upon a second section of a third seal segment, placing a first section of the third seal segment upon a second section of a fourth seal segment and placing a first section of the fourth seal segment upon a second section of the first seal segment.

15. The trocar assembly according to claim 9, wherein each seal segment includes a central curved portion.

16. The trocar assembly according to claim 9, wherein each seal segment is an elastomer of a cross linked polymer.

17. A trocar assembly, comprising:
a trocar cannula including a proximal end and distal end;
a trocar housing coupled to the proximal end of the trocar cannula for receiving and guiding an obturator through the trocar cannula, the trocar housing includes an open proximal end portion defining an opening provided with a proximal seal assembly and a distal seal assembly;
the proximal seal assembly includes:
a plurality of seal segments, each seal segment includes a peripheral edge and a seam edge;
each seal segment further includes a first section and a second section with a vertical wall connecting the first section and the second section in such a way that the first section is displaced and offset relative to the second section such that the first section of a first seal segment may be placed upon the second section of a second seal segment with the first sections of the first and second seal segments lying in the same plane and the second sections of the first and second seal segments lying in the same plane, wherein the vertical walls of the seal segments, with respective first sections and second sections, create two separate sealing surface which are separated with an air space therebetween;
wherein the seal segments are assembled in an overlapping woven arrangement to provide a complete seal body without the need for a secondary seal.

18. The trocar assembly according to claim 17, wherein the peripheral edge of each seal segment defines an arc of approximately 180 degrees.

19. The trocar assembly according to claim 17, wherein the proximal seal assembly includes four individual seal segments combined in a woven arrangement by placing a first section of a first seal segment upon a second section of a second seal segment, placing a first section of the second seal segment upon a second section of a third seal segment, placing a first section of the third seal segment upon a second section of a fourth seal segment and placing a first section of the fourth seal segment upon a second section of the first seal segment.

20. The trocar assembly according to claim 17, wherein each of the seal segments are substantially semi-circular.

* * * * *